United States Patent [19]

Chan

[11] Patent Number: 5,412,182
[45] Date of Patent: May 2, 1995

[54] EDDY CURRENT HEATING FOR HYPERTHERMIA CANCER TREATMENT

[75] Inventor: Kwok W. Chan, Chino Hills, Calif.
[73] Assignee: City of Hope, Duarte, Calif.
[21] Appl. No.: 865,939
[22] Filed: Apr. 9, 1992
[51] Int. Cl.$^6$ ............................................... H05B 6/14
[52] U.S. Cl. ..................................... 219/635; 219/643; 219/670; 219/676; 219/618; 607/116; 607/145; 607/154
[58] Field of Search ............. 219/10.41, 10.57, 10.491, 219/10.75, 635, 643, 670, 674, 676, 618; 128/804; 607/154, 116, 145

[56] References Cited

U.S. PATENT DOCUMENTS

| | | | |
|---|---|---|---|
| 1,918,209 | 7/1933 | Laub | 219/10.75 |
| 3,736,555 | 5/1973 | Barrow | 340/8 |
| 3,991,770 | 11/1976 | Leveen | 128/413 |
| 4,017,701 | 4/1977 | Mittelmann | 219/10.491 |
| 4,082,936 | 4/1978 | Aoki et al. | 219/10.41 |
| 4,263,479 | 4/1981 | Lange et al. | 336/68 |
| 4,527,550 | 7/1985 | Ruggeka et al. | 128/1.5 |
| 4,795,886 | 1/1989 | Carter, Jr. | 219/10.75 |
| 4,872,458 | 10/1989 | Kanehira et al. | 128/401 |
| 4,945,912 | 8/1990 | Langberg | 128/804 |
| 4,975,672 | 12/1990 | McLyman | 336/198 |

Primary Examiner—Philip H. Leung
Attorney, Agent, or Firm—Edward S. Irons

[57] ABSTRACT

An interstitial heater, made of an electrically conductive tube with a wire wound in a toroidal configuration about the tube and connected to a capacitor to form a tank circuit, is driven with a radiofrequency power source at resonance to provide tissue heating by thermal conduction.

4 Claims, 1 Drawing Sheet

EDDY CURRENT HEATING FOR HYPERTHERMIA CANCER TREATMENT

TECHNICAL FIELD

The present invention relates generally to induction of eddy currents in tubings using proximal wire windings for providing hyperthermia cancer treatment. Produced eddy currents in the tube cause the tube to be heated. The winding is tuned with appropriate capacitors as in a tank circuit, and driven at resonance with a radiofrequency source.

BACKGROUND ART

It is known that heating a cancer tumor to about 43° C. can promote regression. Radiation, microwave and other methods of heating tissue have been used to promote tumor regression.

For example, dipole antennas have been inserted in catheters with electromagnetic energy radiated from antenna junctions. Typically such junctions are on the order of 1 mm. Energy radiated from individual antenna junctions may enhance or cancel each other depending on electromagnetic wave propagation characteristics within the tissue. Heating desired tumor locations is achieved through a power adjustment and sometimes phase control of the individual antennas. Because of small radiating antenna junctions, heating is usually limited to a few centimeters within the junction plane along the antennas. Temperature uniformity within such heated tumor volumes is dependent on wave propagation, tissue characteristics, thermal conductivity and blood perfusion rates, all of which are not directly controllable. Therefore this technique is usually limited to tumors of 3–4 cm long.

Use of radiofrequency induced currents with needles is another technique which has previously been attempted. Here, metallic needle pairs (electrodes) are implanted at approximately 1–2 cm spacings into a tumor volume and radiofrequency currents are passed through the electrode pairs. Heating is a function of tissue resistance to current flow between the electrodes which varies with different tissue types. Different techniques have been developed to drive currents through electrode pairs to achieve uniform therapeutic temperatures within tumor volumes. Since heating is a function of the electrical characteristics of tissue between the needle pairs, electrode spacing uniformity is critical. In practical applications where long electrodes are required, it is difficult to maintain necessary uniform spacings and hot spots can result which cause burns or related complications.

Another known technique utilizes stranded or solid wires of selected lengths, approximately 1–2 mm in diameter, inserted in arrays of catheters implanted within a tumor volume. The patient is then placed within an induction coil and exposed to high intensity magnetic fields. Different coil configurations have been used and driven in series or in parallel resonance circuit configurations to generate the required magnetic field. The implants are accordingly heated by resistive loses from any induced current circulations and the tumor tissue is heated by thermal conduction. Implant temperatures are achieved in accordance with Curie temperature characteristics of the ferromagnetic material used. The ferromagnetic property of these implants changes as a function of temperature, heating is gradually reduced as the Curie temperature is approached and further reduced when the Curie temperature is exceeded. Thermal regulation is dependent on a sharp transition in the Curie temperature curve at the desired temperature. The availability of implants that can be thermally regulated at desirable temperatures is limited by practical metallurgy limitations. Further, coils used to generate required high intensity magnetic fields are extremely inefficient. In fact, 1500–3000 Watts can be required and the implants need to be aligned with the applied magnetic field. Due to the high power requirements, both very expensive radiofrequency shielded rooms and complex cooling systems are required.

Yet another known system utilizes implantation of heating elements embedded within the walls of plastic catheters (typically 2.2 mm in diameter) which are then directly inserted into tissue. Heating is accomplished with an array of implanted catheters through thermal conduction. Temperature uniformity is maintained through active control of the current flowing in individual heating elements. Since direct current (dc) is used, the advantages of high frequency effects cannot be realized. Heating is only a function of the applied voltage and current. The technique is simple but there are practical limitations in the maximum voltage and current that can be applied to size limited embedded heating elements. Patient safety and electrical isolation requirements are more difficult to comply with for dc than with high frequency systems. Further, the resistance of heating elements is a function of length which when combined with voltage and current requirements restricts practical therapeutic applications.

Finally, catheters have been implanted in tumor tissue with heated water passed through the catheters to provide hyperthermia. Control of water temperature passing through individual catheters is used to maintain uniform tumor temperature. Clearly a very involved system and process. Further, there are unavoidable difficulties with miniaturized plumbing which limit practical applications. Changes in temperature within the small volume of water passing through the catheters due to thermal conduction results in undesirable temperature non-uniformity along the catheter lengths which additionally limits practical applications.

DISCLOSURE OF THE INVENTION

The present invention utilizes needle tubings implanted in tumors with windings of fine gauge magnet wire about the needle tubes. The windings are connected to appropriately selected capacitors. Eddy currents are induced in the needle tubes when the tank circuit, including the needle tube with winding and the capacitor, is driven at parallel resonance with a power source. The amount of heat generated in the needle tubings due to resistive losses from circulating eddy currents is a function of electrical properties of the needle tubing material, the radius and wall thickness of the tubing and the operating resonance frequency of the tank circuit. At high frequencies, the induced eddy currents are concentrated at the inside and outside surfaces of the tubings. As the effective cross-sectional area of current flow in the tubing decreases its resistance to current flow is increased. Therefore, heating is more effective at higher frequencies because of the increased resistance due to skin depth effect. The amount of energy required to sustain large current flow in the active components of the tank circuit, the capacitor and the winding about the needle tube is very small. Loses are limited to those from the wire used in the winding and the dielectric loss of the capacitor. The magnitude of eddy currents induced in the needle tubings is proportional to the large current flow in the windings and to the proximity of windings to the needle tubing. Both of which are optimized with the present invention. Namely, with wire wound directly on the needle tubing and tuned to parallel resonance at the optimal resonance frequency based on tubing dimensions and material characteristics results in maximized heating due to resistive losses from eddy current circulation.

Heating with the present invention can be optimized by using ferromagnetic materials such as 400 series stainless steel needle tubings. In this case increased eddy current induction is due to high relative permeability of ferromagnetic material which results in more heating.

The needle tubes with toroidally wound wire can be inserted in tumors via arrays of catheters for heating tumor tissues. Interstitial hyperthermia is often used in combination with brachytherapy to enhance the effects of radiation treatments. Different interstitial heating techniques can be used to heat tumor tissues to a therapeutic temperature of approximately 43° C. before or after radiation. Catheters are implanted at 1-2 cm spacings throughout the tumor volume for insertion of radiation sources and interstitial heating implants (or electrodes). Needle tubes with toroidally wound wire can be used as heating sources which through thermal conduction raise tumor tissue to therapeutic temperatures. Active or feedback control of power delivered to windings of individual needle tubings can be used to maintain uniform temperatures within the tumor volume. Active control provides a heating system with the ability to make responsive power adjustments by sampling existing conditions and compensating for continuously changing biological effects, such as blood flow, within the heated tumor. With this eddy current heating technique, an efficient, therefore compact and portable, clinical system can be developed for interstitial hyperthermia applications.

Needle tubes with toroidal windings can be used for applications other than interstitial hyperthermia when small heat sources providing moderate temperatures (up to 120° C.) in tight fitting locations are required.

BRIEF DESCRIPTION OF THE DRAWINGS

The various objectives, advantages and novel features of the present invention will become more readily apprehended from the following detailed description when taken in conjunction with the appended drawings, in which.

BEST MODE FOR CARRYING OUT THE INVENTION

Figure 1:
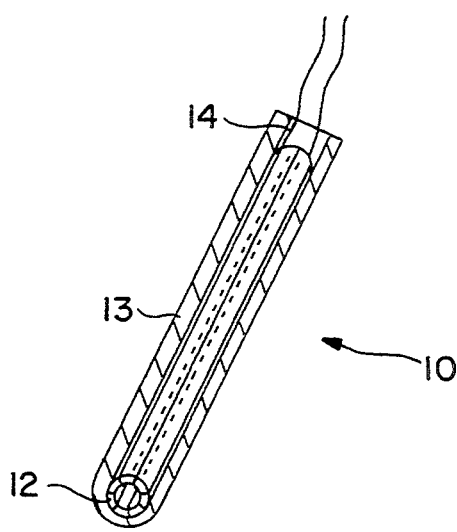
FIG. 1 is a perspective view of a needle tube with toroidal wire winding according to the present invention, the needle is shown in a sectioned tube.

Referring now to the drawings, wherein corresponding components are designated by the same reference numerals throughout the various figures, a perspective view of a needle tubing with associated winding according to the present invention is shown in FIG. 1 where it is generally designated by reference numeral 10.

The needle tube 12 of the eddy current heater 10 of the present invention is preferably made of materials with high relative permeability. So ferromagnetic properties can be taken advantage of to enhance eddy current heating. Stainless steel tubes of 17 gauge, 7 cm long, have been used for the needle tube 12. In particular both Type 304 and 430 stainless steel have been used, but Type 430 is preferred because it is ferromagnetic and provided more heat than the Type 304 which is paramagnetic.

The wire 14 of the eddy current heater 10 of the present invention is preferably 36 or 38 AWG enamel coated copper wire. Typically the wire 14 is wound six times around the longitudinal length of the needle tube 12 in a toroidal configuration.

The eddy current heater 10 is sealed within a thin wall plastic tubing 13 for electrical isolation and protection of the winding.

Figure 2:
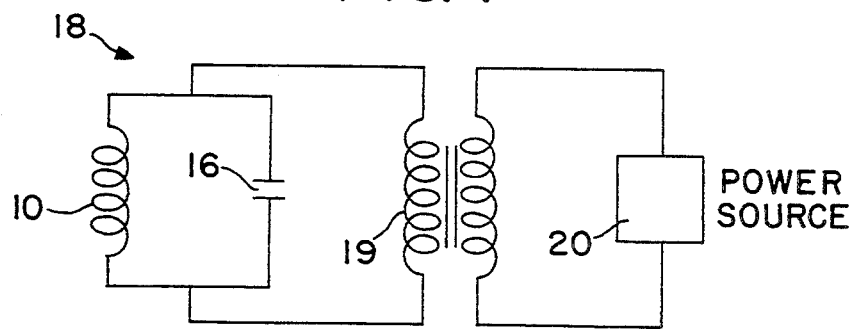
FIG. 2 is a schematic for a circuit showing a tank circuit used to produce eddy currents in the needle tube of the present invention; and, FIG. 3 is a chart plotting Relative Efficiency as a function of the Percent of Optimal Frequency.

Connected across the wire 14 is a capacitor 16. This combination of a wire 14 wound in a toroidal fashion about a needle tube 12 with a capacitor 16 forms a tank circuit generally designated by reference numeral 18, see FIG. 2. Connected between the tank circuit 18 and the power source 20 is an impedance matching transformer 19 that provides optimal power transfer at selected frequencies. To properly use the eddy current heater 10, the power source 20 must be turned to the resonant frequency of the tank circuit 18. It is known that the resonant frequency for a tank circuit is $\frac{1}{2\pi\sqrt{LC}}$: where L is the inductance of the toroidal winding 14 about the needle tube 12; and, C is the capacitance of capacitor 16.

Figure 3:
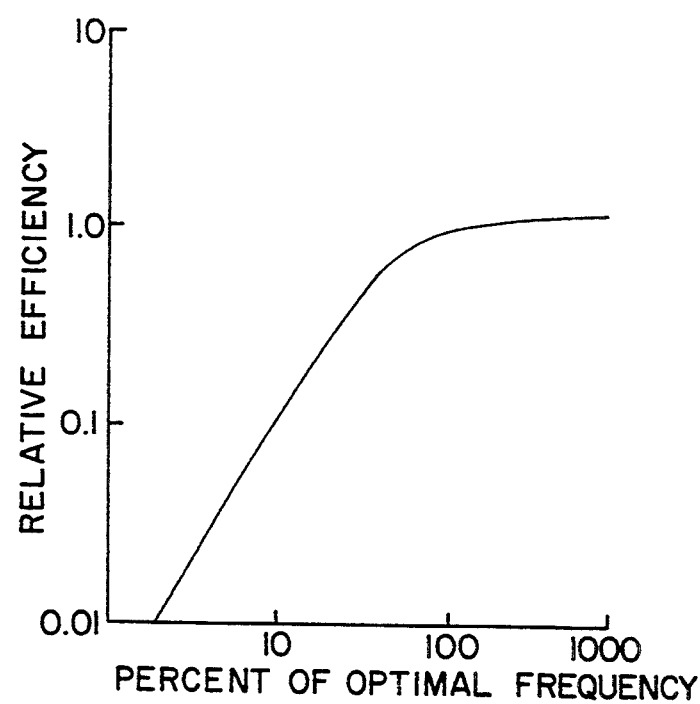

It has been found that heating rates for eddy current heaters 10 are proportional to the coupling efficiency between the toroidal winding 14 and the needle tube 12. Coupling efficiency is a function of the radius, wall thickness and skin depth (electrical current penetration depth) of the needle tubing 12 which varies with the resistivity, permeability and frequency of currents induced in the needle tube 12. For needle tubes 12 of a given material and size, there exists a critical (or an optimal) frequency which provides optimal coupling. Heating improves very little above this frequency and becomes extremely inefficient when operating below it, see FIG. 3.

For arrays of four eddy current heaters 10 of 2×2 at 1.2 cm spacing, heating rates of 0.018°–0188° C./W-min per array were observed in tests along the central axis.

Implants of 1.2 mm diameter can be made with eddy current heaters 10 of the present invention while other techniques require diameters on the order of 2 mm. With a smaller implant diameter there is less tissue trauma, therefore clinically the eddy current heater 10 of the present invention is a better choice.

Variations of eddy current heater 10 can also include:

(i) larger diameter needle tubes 12 for heating intracavitary tumors;

(ii) short sections of needle tubes 12 strung together to create a flexible implant for tumor sites where straight or rigid implants are not possible; and, (iii) semi-circular or flat sections instead of tubular shapes for applications where circumferential heating is not desirable. High permeability ferromagnetic materials can be used instead of non-magnetic materials to generate more heat with the availability of different material characteristics and physical dimensions, the combinations are not limited.

Small tubular ceramic capacitors 16 which fit on the ends of needle tubes 12 can also be used to tune the windings for operation at resonance frequencies. It is possible to have the entire tank circuit within one assembly and losses in feed wires thus minimized.

The above discussion and related illustrations of the present invention are directed primarily to a preferred embodiment and practices of the invention. However, it is believed that numerous changes and modifications in the actual implementation of the concepts described herein will be apparent to those skilled in the art, and it is contemplated that such changes and modifications may be made without departing from the scope of the invention as defined by the following claims.

What is claimed is:

1. A hyperthermia device comprising:
    a length of metallic needle tube,
    a wire wound toroidally around said length of metallic needle tube, and
    means for connecting a power source to said wire,
    wherein said length of metallic needle tube is heated by eddy currents produced therein when an energized power source is connected to said wire.

2. A hyperthermia device:
    said device being sealed in electrically insulating plastic tubing,
    said device comprising:
        a length of metallic needle tube,
        a wire wound toroidally around said length of metallic needle tube, and
        means for connecting a power source to said wire,
        wherein said length of metallic needle tube is heated by eddy currents produced therein when an energized power source is connected to said wire.

3. The hyperthermia device of claim 1 or claim 2 in which said length of metallic needle tube is a length of seventeen gauge stainless steel needle tube and in which said wire is 36 or 38 AWG enamel coated copper wire.

4. A hyperthermia device comprising:
    a length of metallic needle tube,
    a wire wound toroidally around said length of metallic needle tube,
    a capacitor connected across said wire to form a tank circuit,
    a power source, and
    an impedance matching transformer connected between said tank circuit and said power source,
    wherein said length of metallic needle tube is heated by eddy currents produced therein when said power source is energized.

* * * * *